(12) United States Patent
Falco et al.

(10) Patent No.: US 6,297,055 B1
(45) Date of Patent: Oct. 2, 2001

(54) AMINO ACID DECARBOXYLASES

(75) Inventors: Saverio Carl Falco, Arden; Layo O. Famodu, Newark, both of DE (US); Emil M. Orozco, Jr., West Grove, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/377,557

(22) Filed: Aug. 19, 1999

Related U.S. Application Data

(60) Provisional application No. 60/099,493, filed on Sep. 8, 1998, now abandoned.

(51) Int. Cl.[7] .............................. C12N 5/04; C12N 5/06; C12N 15/29; C12N 15/52; C12N 15/82
(52) U.S. Cl. ...................... 435/468; 435/320.1; 435/419; 435/471; 536/23.6
(58) Field of Search ................................ 435/69.1, 320.1, 435/468, 410, 419, 471; 536/23.6, 23.1, 23.2; 800/278, 295, 298

(56) References Cited

PUBLICATIONS

Park et al. (1996) Mol. Microbiol. 20:605–611.
Lemonnier and Lane (1998) Microbiology 144:751–760.
Kim et al. (1998) Arch. Biochem. Biophys. 354:40–46.
Koch et al. (1998) Development 125:2303–2313.
Facchini and DeLuca (1994) J. Biol. Chem. 269:26684–26690.
Kawalleck et al. (1993) J. Biol. Chem. 268:2189–2194.
Goddijn et al. (1995) Transgenic Res. 4:315–323.
Lopez–Mever and Nessler (1997) Plant J. 11:1167–1175.
NCBI General Identifier No. 1651862.
Raneko et al DNA Res. 3, 109–136 (1996).
NCBI General Identifier No. 1174828.
NCBI General Identifier No. 3282523.
NCBI General Identifier No. 4512701.
NCBI General Identifier No. 118306.
De Luca et al Proc. Natl. Acad. Sci. 86(8), 2582–2586 (1989).
Goddjn et al Mol. Gen. Genet. 242(2), 217–225 (1994).
Heerze et al. (1990) Anal. Biochem. 185:201–205.
Burns and Aberhart (1988) Anal Biochem. 171:339–345.

*Primary Examiner*—Gary Benzion
*Assistant Examiner*—Ashwin S. Mehta

(57) ABSTRACT

This invention relates to an isolated nucleic acid fragment encoding an amino acid decarboxylase. The invention also relates to the construction of a chimeric gene encoding all or a portion of the amino acid decarboxylase, in sense or antisense orientation, wherein expression of the chimeric gene results in production of altered levels of the amino acid decarboxylase in a transformed host cell.

8 Claims, No Drawings

SEQUENCE LISTING

<160> NUMBER OF SEQ ID NOS: 20

<210> SEQ ID NO 1
<211> LENGTH: 625
<212> TYPE: DNA
<213> ORGANISM: Catalpa speciosa
<220> FEATURE:
<221> NAME/KEY: unsure
<222> LOCATION: (275)
<220> FEATURE:
<221> NAME/KEY: unsure
<222> LOCATION: (287)
<220> FEATURE:
<221> NAME/KEY: unsure
<222> LOCATION: (315)
<220> FEATURE:
<221> NAME/KEY: unsure
<222> LOCATION: (329)
<220> FEATURE:
<221> NAME/KEY: unsure
<222> LOCATION: (384)
<220> FEATURE:
<221> NAME/KEY: unsure
<222> LOCATION: (419)
<220> FEATURE:
<221> NAME/KEY: unsure
<222> LOCATION: (434)
<220> FEATURE:
<221> NAME/KEY: unsure
<222> LOCATION: (447)
<220> FEATURE:
<221> NAME/KEY: unsure
<222> LOCATION: (470)..(471)
<220> FEATURE:
<221> NAME/KEY: unsure
<222> LOCATION: (479)
<220> FEATURE:
<221> NAME/KEY: unsure
<222> LOCATION: (500)
<220> FEATURE:
<221> NAME/KEY: unsure
<222> LOCATION: (502)
<220> FEATURE:
<221> NAME/KEY: unsure
<222> LOCATION: (505)
<220> FEATURE:
<221> NAME/KEY: unsure
<222> LOCATION: (512)
<220> FEATURE:
<221> NAME/KEY: unsure
<222> LOCATION: (514)
<220> FEATURE:
<221> NAME/KEY: unsure
<222> LOCATION: (519)
<220> FEATURE:
<221> NAME/KEY: unsure
<222> LOCATION: (522)
<220> FEATURE:
<221> NAME/KEY: unsure
<222> LOCATION: (532)
<220> FEATURE:
<221> NAME/KEY: unsure
<222> LOCATION: (540)
<220> FEATURE:
<221> NAME/KEY: unsure
<222> LOCATION: (549)
<220> FEATURE:
<221> NAME/KEY: unsure
<222> LOCATION: (564)
<220> FEATURE:
<221> NAME/KEY: unsure
<222> LOCATION: (568)
<220> FEATURE:
<221> NAME/KEY: unsure
<222> LOCATION: (575)
<220> FEATURE:

<221> NAME/KEY: unsure
<222> LOCATION: (578)..(579)
<220> FEATURE:
<221> NAME/KEY: unsure
<222> LOCATION: (588)
<220> FEATURE:
<221> NAME/KEY: unsure
<222> LOCATION: (590)
<220> FEATURE:
<221> NAME/KEY: unsure
<222> LOCATION: (597)..(598)
<220> FEATURE:
<221> NAME/KEY: unsure
<222> LOCATION: (608)
<220> FEATURE:
<221> NAME/KEY: unsure
<222> LOCATION: (621)

<400> SEQUENCE: 1

```
gggacagcat gagagtttag catttgactc aacacacaat gtgatccata aaggttctca    60
gaaagtcgag aattgtagac tccctcctct ggtttgtgca ctaaaagctt cagcagaaga   120
aaacgcagcc agttttcact ttccaggaca taacagagga caagctgctc cattgtcatt   180
gactcagctg atcggtgcaa gaccgtttca gcatgactta ccagaacttc caagagctcc   240
gacaatcttt tgctcctga aggggcctat tttangaagc acagcangag gcagccaaac   300
tttttgggag catcnggaga catggtccnt gtggggtggg cagtacatgt gggtgtccaa   360
ggcaagcata atgggactg ttcnacctgg gagacatccc atcctcctcg aaatctcana   420
tttctgcagt accnccatgg gataacnggg gcctaccaag taatatcccn nacaatganc   480
tgaagggaat acgggggcan anccnttcac antngagana ancaagggct tnaacggggn   540
caaaacacnc gtttggcatt accnaatncc ggatncanna atgggcantn aagcggnnaa   600
ccaaatcnat atttgggggc ncggg                                         625
```

<210> SEQ ID NO 2
<211> LENGTH: 127
<212> TYPE: PRT
<213> ORGANISM: Catalpa speciosa

<400> SEQUENCE: 2

```
Pro Leu Val Cys Ala Leu Lys Ala Ser Ala Glu Glu Asn Ala Ala Ser
 1               5                  10                  15
Phe His Phe Pro Gly His Asn Arg Gly Gln Ala Ala Pro Leu Ser Leu
                20                  25                  30
Thr Gln Leu Ile Gly Ala Arg Pro Phe Gln His Asp Leu Pro Glu Leu
            35                  40                  45
Pro Glu Leu Asp Asn Leu Phe Ala Pro Glu Gly Pro Ile Leu Glu Ala
        50                  55                  60
Gln Gln Glu Ala Ala Lys Leu Phe Gly Ala Ser Glu Thr Trp Phe Leu
    65                  70                  75                  80
Val Gly Gly Ser Thr Cys Gly Val Gln Ala Ala Ile Met Ala Thr Cys
                85                  90                  95
Ser Pro Gly Asp Thr Pro Ile Leu Pro Arg Asn Ser His Ile Ser Ala
               100                 105                 110
Val Ser Ala Met Gly Ile Asn Gly Gly Arg Thr Gln Leu Ile Ile
           115                 120                 125
```

<210> SEQ ID NO 3
<211> LENGTH: 1867
<212> TYPE: DNA
<213> ORGANISM: Zea mays

-continued

<400> SEQUENCE: 3

```
cacccacgcg tccggccgtc tgagggaagc agggcgcagc agtcaccagt gaccagtcat     60
ggctcgctgc gttgccggca gctgccctcc cgtcaccttc gcgtgttgcc cccgccggac    120
tggacgaagt gctgttgttc agtgtggcac tgcatcgagc acaccagcaa tatctggaac    180
cggaccttca tcatctggat cctcggggct tgttcaagat tgtactgccc ctctggtctg    240
tgcactgcaa ttaactgcca gacaagatgt ttcctgcttt cacttcccag gacacaacag    300
aggaaaagct gctccatctt ccttgtcgaa actcattggc tcagggcat ttctgcatga     360
cttgcccgag ctaccgagc tcgatgatct cttctcccca aaggtgtga ttctagatgc       420
ccagaggcga gcagctcaac tgtttgggtc atctaaaact tggttccttg tcaacggaac    480
gacctgtgga atccaggcct cagtgatggc tacctgttct cctggcgact acctcattgt    540
gccacggaac tgccaccttt cagtgatctc tgcgctggtc ttgtctggtg tggtgcctaa    600
atacataata ccagaatata attctgggtg ggacattgct ggtggtatca ccccgctgca    660
gctggatgaa gcagtaaaag agctggagga ggatgggaag agggtaggcg ctgttcttgt    720
tacttcaccc acctaccatg gtgtatgcag caatgtgcaa ggtattgtca gtgtttgtca    780
tccacgaggc attccggtta tagttgatga gcgcatggt gcacatttca ggttccatga     840
cagtttgcca agcactgcaa ttgagcaagg tgctgaccta gctgtgcaat ccacacacaa    900
ggtcctgtgc tccttacac agtcttcaat gcttcacatg tctggagatc ttgtcgatgt     960
agataaagta agccagtgcc ttcagctcct ccagagctcg agcccgagtt accttctact   1020
gtcatcttta gatgccgcga gagatcagct gagccagaac acaaatatat ttgatgagcc   1080
attagctata gcatcggaaa caaaagacct gctggcgaga atccctggga tatctgttct   1140
agacttacca tgctttgctt ctgatttccc tgccattgat ccgttgcgca tcacactcag   1200
tgcctcagat ctgcaattat cgggatacga agccgatgac atttatatg aaggccatca   1260
aatcgtatct gagcttgttg gcacaagggc cgtgacattt gcagtcaact taggaaccag    1320
agtgcaggac gctgagaagc ttgtgcagtc tgcaaagcat ctatcagaaa acatttctt     1380
tgcaaatagc ctgaaacccg tgaaggagaa tcgtgtgcat ggcccattag agaatatctc   1440
tgtgcatctg agtccaagag aggccttctt tacagagaag aggagagtga aaatcgagga   1500
cagccttggt gaaatctgtg gtgagctaat atgcccgtat ccacctggta tcccagttct   1560
gattccaggc gaggtagtaa cccatgattc actgtcctac ttgatgagcg ttagacacca   1620
aggcatcacg atcagtggag cggctgatgc tgagctaaat tccattctgg tgtgcgactt   1680
atgatgattg ccctattgtt tgtcacaaga ctgtgttgtc gcagagatac cgtgggtggg   1740
agagatcaag tatggtttat gccaagtcaa gagcacaatg tattgtccgc ttgatggatg   1800
taaaccaacg gctggcggtt tgtagccacc ggccacttgg ccaaataatt tagtctgtgt   1860
tgtgttg                                                             1867
```

<210> SEQ ID NO 4
<211> LENGTH: 484
<212> TYPE: PRT
<213> ORGANISM: Zea mays

<400> SEQUENCE: 4

```
Pro Leu Val Cys Ala Leu Gln Leu Thr Ala Arg Gln Asp Val Ser Cys
  1               5                  10                  15

Phe His Phe Pro Gly His Asn Arg Gly Lys Ala Ala Pro Ser Ser Leu
```

```
              20                  25                  30
Ser Lys Leu Ile Gly Ser Gly Ala Phe Leu His Asp Leu Pro Glu Leu
        35                  40                  45

Pro Glu Leu Asp Asp Leu Phe Ser Pro Lys Gly Val Ile Leu Asp Ala
    50                  55                  60

Gln Arg Ala Ala Gln Leu Phe Gly Ser Ser Lys Thr Trp Phe Leu
65                  70                  75                  80

Val Asn Gly Thr Thr Cys Gly Ile Gln Ala Ser Val Met Ala Thr Cys
                85                  90                  95

Ser Pro Gly Asp Tyr Leu Ile Val Pro Arg Asn Cys His Leu Ser Val
                100                 105                 110

Ile Ser Ala Leu Val Leu Ser Gly Val Val Pro Lys Tyr Ile Ile Pro
            115                 120                 125

Glu Tyr Asn Ser Gly Trp Asp Ile Ala Gly Ile Thr Pro Leu Gln
        130                 135                 140

Leu Asp Glu Ala Val Lys Glu Leu Glu Glu Asp Gly Lys Arg Val Gly
145                 150                 155                 160

Ala Val Leu Val Thr Ser Pro Thr Tyr His Gly Val Cys Ser Asn Val
                165                 170                 175

Gln Gly Ile Val Ser Val Cys His Pro Arg Gly Ile Pro Val Ile Val
            180                 185                 190

Asp Glu Ala His Gly Ala His Phe Arg Phe His Asp Ser Leu Pro Ser
                195                 200                 205

Thr Ala Ile Glu Gln Gly Ala Asp Leu Ala Val Gln Ser Thr His Lys
        210                 215                 220

Val Leu Cys Ser Leu Thr Gln Ser Ser Met Leu His Met Ser Gly Asp
225                 230                 235                 240

Leu Val Asp Val Asp Lys Val Ser Gln Cys Leu Gln Leu Leu Gln Ser
                245                 250                 255

Ser Ser Pro Ser Tyr Leu Leu Leu Ser Ser Leu Asp Ala Ala Arg Asp
                260                 265                 270

Gln Leu Ser Gln Asn Thr Asn Ile Phe Asp Glu Pro Leu Ala Ile Ala
        275                 280                 285

Ser Glu Thr Lys Asp Leu Leu Ala Arg Ile Pro Gly Ile Ser Val Leu
    290                 295                 300

Asp Leu Pro Cys Phe Ala Ser Asp Phe Pro Ala Ile Asp Pro Leu Arg
305                 310                 315                 320

Ile Thr Leu Ser Ala Ser Asp Leu Gln Leu Ser Gly Tyr Glu Ala Asp
                325                 330                 335

Asp Ile Leu Tyr Glu Gly His Gln Ile Val Ser Glu Leu Val Gly Thr
                340                 345                 350

Arg Ala Val Thr Phe Ala Val Asn Leu Gly Thr Arg Val Gln Asp Ala
        355                 360                 365

Glu Lys Leu Val Gln Ser Ala Lys His Leu Ser Glu Lys His Phe Phe
    370                 375                 380

Ala Asn Ser Leu Lys Pro Val Lys Glu Asn Arg Val His Gly Pro Leu
385                 390                 395                 400

Glu Asn Ile Ser Val His Leu Ser Pro Arg Glu Ala Phe Phe Thr Glu
                405                 410                 415

Lys Arg Arg Val Lys Ile Glu Asp Ser Leu Gly Glu Ile Cys Gly Glu
                420                 425                 430

Leu Ile Cys Pro Tyr Pro Pro Gly Ile Pro Val Leu Ile Pro Gly Glu
        435                 440                 445
```

-continued

Val Val Thr His Asp Ser Leu Ser Tyr Leu Met Ser Val Arg His Gln
        450                 455                 460

Gly Ile Thr Ile Ser Gly Ala Ala Asp Ala Glu Leu Asn Ser Ile Leu
465                 470                 475                 480

Val Cys Asp Leu

<210> SEQ ID NO 5
<211> LENGTH: 1321
<212> TYPE: DNA
<213> ORGANISM: Glycine max

<400> SEQUENCE: 5

| | | | | | |
|---|---|---|---|---|---|
| gcaccagatc | acctcaccta | cttatcatgc | cctccagcaa | ggagctgatc | tgactgtaca | 60 |
| gtctactcac | aaagttctat | gctctctgac | tcagtcatct | atgctgcaca | gtcgggaaa | 120 |
| tattgtagat | aaggaaaaaa | tttctagatg | tctccaaact | cttcaatcca | aagccctag | 180 |
| ttatctgctt | ttggcatctc | tggatgctgc | tagagctcaa | cttagtgaaa | gccctgatgt | 240 |
| tgtattcaac | caagcaatgg | cattagctta | tgaggcaaag | tgcatgctaa | acgaatccc | 300 |
| tggtatatca | gtgcttgaga | attcaagctt | ccaaccttt | cctgcaattg | atccattgcg | 360 |
| tctcactgtg | ggttttttgga | aggttggttt | atcaggttat | gaagcagacg | aaatcctata | 420 |
| tggagattac | ggggtagtct | gtgaacttgt | tgggaataaa | tctattactt | atgcattcaa | 480 |
| tcttggaact | tgtagggacc | atgtccaaag | gcttttatca | ggaataaagc | atttggctgc | 540 |
| aacatatgtt | accattcagc | aacctgaaga | gagagtgctt | acagttcatg | caccctttga | 600 |
| tgataaaatc | acgagtttga | tccctagaga | tgcctttttt | gcaagtaaaa | gaatagtaac | 660 |
| gataaaggag | agcatcggtg | agatttcagg | ggagcttata | tgtccatacc | ctccgggcat | 720 |
| accagtatta | atccccggcg | aggttattac | caaaaaagct | gttgattatc | ttcttcatgt | 780 |
| taggagtaaa | ggtggtgata | ttactggagc | atctgatccc | ttactttctt | caatagttgt | 840 |
| ttgcaatgta | tagtaagtaa | atcagctggg | ctgaagcatc | ttgaagttga | aacttcccaa | 900 |
| gttggacttt | ggtctttctg | cacaccatat | ggttagacaa | agatttccac | agttggagga | 960 |
| attctcaagt | tggtagcaac | tactaatggc | tgtactaaag | tcggtaacta | ttctctcatt | 1020 |
| ttaatgggta | aaagcaaaat | agttttgaat | tttcgtctct | tgaaaattct | gctggattcc | 1080 |
| ccgagcgtta | aatgtagttc | caaaccattg | ggaaagaaat | gtcatgacac | agggcaatat | 1140 |
| agcgtcaatc | cttatcgaag | gactgaaatt | atgggcaaag | ctcagaagca | aaccagcaac | 1200 |
| tacctggaaa | aagccataaa | tataaaaaga | aaatgacaac | taattgaatt | tttaagttta | 1260 |
| tatttagaga | atgttatgga | agaatagaag | gattgattta | tataaaattt | tcatgatttt | 1320 |
| t | | | | | | 1321 |

<210> SEQ ID NO 6
<211> LENGTH: 283
<212> TYPE: PRT
<213> ORGANISM: Glycine max

<400> SEQUENCE: 6

His Gln Ile Thr Ser Pro Thr Tyr His Ala Leu Gln Gln Gly Ala Asp
 1               5                  10                  15

Leu Thr Val Gln Ser Thr His Lys Val Leu Cys Ser Leu Thr Gln Ser
                20                  25                  30

Ser Met Leu His Met Ser Gly Asn Ile Val Asp Lys Glu Lys Ile Ser
         35                  40                  45

```
Arg Cys Leu Gln Thr Leu Gln Ser Thr Ser Pro Ser Tyr Leu Leu Leu
         50                  55                  60

Ala Ser Leu Asp Ala Ala Arg Ala Gln Leu Ser Glu Ser Pro Asp Val
 65                  70                  75                  80

Val Phe Asn Gln Ala Met Ala Leu Ala Tyr Glu Ala Lys Cys Met Leu
                 85                  90                  95

Lys Arg Ile Pro Gly Ile Ser Val Leu Glu Asn Ser Ser Phe Pro Thr
                100                 105                 110

Phe Pro Ala Ile Asp Pro Leu Arg Leu Thr Val Gly Phe Trp Lys Val
            115                 120                 125

Gly Leu Ser Gly Tyr Glu Ala Asp Glu Ile Leu Tyr Gly Asp Tyr Gly
        130                 135                 140

Val Val Cys Glu Leu Val Gly Asn Lys Ser Ile Thr Tyr Ala Phe Asn
145                 150                 155                 160

Leu Gly Thr Cys Arg Asp His Val Gln Arg Leu Leu Ser Gly Ile Lys
                165                 170                 175

His Leu Ala Ala Thr Tyr Val Thr Ile Gln Gln Pro Glu Glu Arg Val
            180                 185                 190

Leu Thr Val His Ala Pro Phe Asp Asp Lys Ile Thr Ser Leu Ile Pro
        195                 200                 205

Arg Asp Ala Phe Phe Ala Ser Lys Arg Ile Val Thr Ile Lys Glu Ser
210                 215                 220

Ile Gly Glu Ile Ser Gly Glu Leu Ile Cys Pro Tyr Pro Pro Gly Ile
225                 230                 235                 240

Pro Val Leu Ile Pro Gly Glu Val Ile Thr Lys Lys Ala Val Asp Tyr
                245                 250                 255

Leu Leu His Val Arg Ser Lys Gly Gly Asp Ile Thr Gly Ala Ser Asp
            260                 265                 270

Pro Leu Leu Ser Ser Ile Val Val Cys Asn Val
        275                 280
```

<210> SEQ ID NO 7
<211> LENGTH: 460
<212> TYPE: DNA
<213> ORGANISM: Zea mays
<220> FEATURE:
<221> NAME/KEY: unsure
<222> LOCATION: (15)
<220> FEATURE:
<221> NAME/KEY: unsure
<222> LOCATION: (107)
<220> FEATURE:
<221> NAME/KEY: unsure
<222> LOCATION: (287)
<220> FEATURE:
<221> NAME/KEY: unsure
<222> LOCATION: (382)
<220> FEATURE:
<221> NAME/KEY: unsure
<222> LOCATION: (419)
<220> FEATURE:
<221> NAME/KEY: unsure
<222> LOCATION: (433)
<220> FEATURE:
<221> NAME/KEY: unsure
<222> LOCATION: (444)

<400> SEQUENCE: 7
gcggacgctg gaggngacca ggaaatgcac ctccacagga ctcctgcttg ctcgacgcag    60
acgagttccg ccggcagggc caccaagtca tcgacttcat cgccgantac tacggccgca   120

```
tggacgacta ccccgtgcac cccagtgtca accccggctt cctgcgccgc cagctccccg      180
acaaggcgcc gtcgcgtccg gagtcgtccg acgcgttcgg tgccgcgctg cgggacgtcc      240
gtgacctcat cctgccaggc atgacgcact ggcagagcgc ccgccanttc gcgcacttcc      300
cggcgtccag cagcaccgtc ggcgccctcg gcgaggccct caaggccggc atcaactccg      360
tccctttcaa gtgggccgcc tngccggccg ccaaggagct cgagatggtc gtcgttgant      420
gggtcggcaa agngctccaa ctgnccgaga gctaatgttt                            460
```

<210> SEQ ID NO 8
<211> LENGTH: 134
<212> TYPE: PRT
<213> ORGANISM: Zea mays
<220> FEATURE:
<221> NAME/KEY: UNSURE
<222> LOCATION: (19)
<220> FEATURE:
<221> NAME/KEY: UNSURE
<222> LOCATION: (79)
<220> FEATURE:
<221> NAME/KEY: UNSURE
<222> LOCATION: (111)
<220> FEATURE:
<221> NAME/KEY: UNSURE
<222> LOCATION: (123)
<220> FEATURE:
<221> NAME/KEY: UNSURE
<222> LOCATION: (128)
<220> FEATURE:
<221> NAME/KEY: UNSURE
<222> LOCATION: (132)

<400> SEQUENCE: 8

```
Leu Asp Ala Asp Glu Phe Arg Arg Gln Gly His Gln Val Ile Asp Phe
 1               5                  10                  15

Ile Ala Xaa Tyr Tyr Gly Arg Met Asp Asp Tyr Pro Val His Pro Ser
            20                  25                  30

Val Asn Pro Gly Phe Leu Arg Arg Gln Leu Pro Asp Lys Ala Pro Ser
        35                  40                  45

Arg Pro Glu Ser Ser Asp Ala Phe Gly Ala Ala Leu Arg Asp Val Arg
    50                  55                  60

Asp Leu Ile Leu Pro Gly Met Thr His Trp Gln Ser Ala Arg Xaa Phe
65                  70                  75                  80

Ala His Phe Pro Ala Ser Ser Ser Thr Val Gly Ala Leu Gly Glu Ala
                85                  90                  95

Leu Lys Ala Gly Ile Asn Ser Val Pro Phe Lys Trp Ala Ala Xaa Pro
            100                 105                 110

Ala Ala Lys Glu Leu Glu Met Val Val Val Xaa Trp Val Gly Lys Xaa
        115                 120                 125

Leu Gln Leu Xaa Glu Ser
    130
```

<210> SEQ ID NO 9
<211> LENGTH: 1857
<212> TYPE: DNA
<213> ORGANISM: Oryza sativa

<400> SEQUENCE: 9

```
gcacgaggtt ctaacccgcg gccggactgc aactgtaacc caattcctcc tcctcctcg       60 atcaccatgg agggagttgg cggcggcggc ggcggtgagg agtggctgcg gccgatggac     120
gcggagcagc tgcgggagtg cgggcaccgg atggtggatt tcgtcgccga ctactacaaa    180
```

-continued

```
tccatcgagg ccttccccgt cctcagccaa gtccagccag gatatctgaa ggaagttctt    240
ccagattcag ccccaagaca acctgatact ttggattccc ttttttgatga tattcaacaa   300 aaaataatac caggagtaac gcactggcaa agtccaaatt attttgctta ctatccttca    360
aatagcagca ctgctggatt cctggggggag atgcttagtg ctgcctttaa cattgttggc   420
ttcagttgga taacctctcc tgctgctact gagctagagg ttatagtctt agactggttt    480
gcaaaaatgc tccagcttcc aagccagttt ctgtcaactg ctcttggtgg aggagtaata   540
caaggtactg ccagtgaagc tgttcttgtt gcactattgg ctgcacgaga tagagcttta    600
aagaagcatg ggaagcattc ccttgaaaag ttagtagttt atgcatctga ccagacacat    660
tctgctctac aaaaggcatg ccagattgca ggaattttct cagagaatgt tagggttgta    720
attgctgatt gtaataagaa ctacgccgtt gcccctgagg cagttagtga ggcgctttcc    780
atagacctgt catctggttt gataccattt ttcatctgtg caacagtagg tacaacatca    840
tcatcagctg tggaccccct gcctgaacta ggacagatag caaagtccaa tgacatgtgg    900
ttccatattg atgccgcata tgctggaagt gcttgtatat gcccagagta ccgacaccac    960
ctcaatggag tggaagaagc tgattcgttt aatatgaatg cccacaaatg gttcctcact   1020
aacttcgatt gttccttgct atgggttaag gacaggagtt ttctcataca atcattgtct   1080
acgaatccag agtttctcaa aaacaaggct tcccaagcta attcagttgt tgatttcaaa   1140
gattggcaaa ttccacttgg acgacgcttt agatcactta agctatggat ggtcttgaga   1200
ctttatggtg tggacaacct acaaagctat atccggaaac acatacattt ggctgaacat   1260
tttgagcaac ttttattatc tgattcaaga tttgaggtag tgactccaag gacttttttca  1320 cttgtttgtt tccgacttgt gcctcccact tctgaccatg aaaatggacg taaattgaat   1380
tacgatatga tggatggtgt aaattcaagt ggaaagatct tcctatctca cacggttctt   1440
tcaggtaagt tcgtcttgag atttgcagta ggagcgccac ttacagagga gcgacacgtg   1500
gatgccgctt ggaagcttct acgagatgag gccaccaagg tcttggggaa aatggtgtag   1560
ataagtgaat accgctcact gattcagctc attgtttgcc cttcgagtat tgaaggtgcc   1620
aaagttcata caaaaagttt ctgttaagga caatacacga tagcataatt tattcagttg   1680
tgaaacagaa atactgaata ctttctatga ttcttttagt gggttaggtc gtttgatcga   1740
cctgcaattt ttttcgagtt gatattaaac tccctgcatt atggatggta gtgtgaggtg   1800
gcatgcagta taacatttaa catacaaatt ttaccaaaaa aaaaaaaaaa aaaaaaa      1857
```

<210> SEQ ID NO 10
<211> LENGTH: 497
<212> TYPE: PRT
<213> ORGANISM: Oryza sativa

<400> SEQUENCE: 10

```
Met Glu Gly Val Gly Gly Gly Gly Gly Glu Glu Trp Leu Arg Pro
 1               5                  10                  15

Met Asp Ala Glu Gln Leu Arg Glu Cys Gly His Arg Met Val Asp Phe
            20                  25                  30

Val Ala Asp Tyr Tyr Lys Ser Ile Glu Ala Phe Pro Val Leu Ser Gln
        35                  40                  45

Val Gln Pro Gly Tyr Leu Lys Glu Val Leu Pro Asp Ser Ala Pro Arg
    50                  55                  60

Gln Pro Asp Thr Leu Asp Ser Leu Phe Asp Asp Ile Gln Gln Lys Ile
65                  70                  75                  80
```

-continued

```
Ile Pro Gly Val Thr His Trp Gln Ser Pro Asn Tyr Phe Ala Tyr Tyr
                 85                  90                  95
Pro Ser Asn Ser Ser Thr Ala Gly Phe Leu Gly Glu Met Leu Ser Ala
            100                 105                 110
Ala Phe Asn Ile Val Gly Phe Ser Trp Ile Thr Ser Pro Ala Ala Thr
        115                 120                 125
Glu Leu Glu Val Ile Val Leu Asp Trp Phe Ala Lys Met Leu Gln Leu
    130                 135                 140
Pro Ser Gln Phe Leu Ser Thr Ala Leu Gly Gly Val Ile Gln Gly
145                 150                 155                 160
Thr Ala Ser Glu Ala Val Leu Val Ala Leu Leu Ala Ala Arg Asp Arg
                165                 170                 175
Ala Leu Lys Lys His Gly Lys His Ser Leu Glu Lys Leu Val Val Tyr
            180                 185                 190
Ala Ser Asp Gln Thr His Ser Ala Leu Gln Lys Ala Cys Gln Ile Ala
        195                 200                 205
Gly Ile Phe Ser Glu Asn Val Arg Val Val Ile Ala Asp Cys Asn Lys
    210                 215                 220
Asn Tyr Ala Val Ala Pro Glu Ala Val Ser Glu Ala Leu Ser Ile Asp
225                 230                 235                 240
Leu Ser Ser Gly Leu Ile Pro Phe Phe Ile Cys Ala Thr Val Gly Thr
                245                 250                 255
Thr Ser Ser Ser Ala Val Asp Pro Leu Pro Glu Leu Gly Gln Ile Ala
            260                 265                 270
Lys Ser Asn Asp Met Trp Phe His Ile Asp Ala Ala Tyr Ala Gly Ser
        275                 280                 285
Ala Cys Ile Cys Pro Glu Tyr Arg His His Leu Asn Gly Val Glu Glu
    290                 295                 300
Ala Asp Ser Phe Asn Met Asn Ala His Lys Trp Phe Leu Thr Asn Phe
305                 310                 315                 320
Asp Cys Ser Leu Leu Trp Val Lys Asp Arg Ser Phe Leu Ile Gln Ser
                325                 330                 335
Leu Ser Thr Asn Pro Glu Phe Leu Lys Asn Lys Ala Ser Gln Ala Asn
            340                 345                 350
Ser Val Val Asp Phe Lys Asp Trp Gln Ile Pro Leu Gly Arg Arg Phe
        355                 360                 365
Arg Ser Leu Lys Leu Trp Met Val Leu Arg Leu Tyr Gly Val Asp Asn
    370                 375                 380
Leu Gln Ser Tyr Ile Arg Lys His Ile His Leu Ala Glu His Phe Glu
385                 390                 395                 400
Gln Leu Leu Leu Ser Asp Ser Arg Phe Glu Val Val Thr Pro Arg Thr
                405                 410                 415
Phe Ser Leu Val Cys Phe Arg Leu Val Pro Pro Thr Ser Asp His Glu
            420                 425                 430
Asn Gly Arg Lys Leu Asn Tyr Asp Met Met Asp Gly Val Asn Ser Ser
        435                 440                 445
Gly Lys Ile Phe Leu Ser His Thr Val Leu Ser Gly Lys Phe Val Leu
    450                 455                 460
Arg Phe Ala Val Gly Ala Pro Leu Thr Glu Arg His Val Asp Ala
465                 470                 475                 480
Ala Trp Lys Leu Leu Arg Asp Glu Ala Thr Lys Val Leu Gly Lys Met
                485                 490                 495
Val
```

<210> SEQ ID NO 11
<211> LENGTH: 1563
<212> TYPE: DNA
<213> ORGANISM: Glycine max

<400> SEQUENCE: 11

```
gcacgagaat atagccaact atccagtgtt gagtcaagta gaacctggtt atcttagaga      60
actcatgcca tattttgccc ctctcaaccc tgaaccaatt gaaaccatcc ttcaagattt     120
gcagcaacac atagtccctg cattactca ctggcaaagc cctaattact ttgcatactt     180
tccctccagt ggtagcacag cagggtttct aggtgagatg ctgagcacag ggttcaactt     240
ggtagggttc aattgggtgt cttcaccagc tgcaactgag ctagaaagca ctgtcatgga     300
ctggctaggt caggttctga agctcccaaa ggcttttctc ttttcaggta gtggtggagg     360
tgtgttgtta ggtacaactt gtgaggccat tttggtcaca ctagttgctg ctagggataa     420
agtacttggc caaattggta gagaaaatat ttgcaagctg gttgtttatg tctctgatca     480
aacacattgt gctgttcaga aagcagctca cataatagga attcaccaca aaatattag     540
ggctgtcaag actatgaagt caacttcatt cactttgctg ccagagtcac tgttatctgc     600
cattcacaca gatgttcaaa acgggttggt tccttgctat ctttgtgcca ctgtgggcac     660
aacttcaacc actgcagttg atccattagg accactgtgc aaggtggcaa agaatatgg     720
catgtgggtc catgttgatg ctgcttatgc tggaagtgca tgcatttgtc ctgagttcag     780
acacttgatt gatggagttg agggtgcaaa ctcttttagc ctcaatgctc acaagtggtt     840
tctcactaac ttagattgtt gctgtctttg gctgaaggat ccagcttctg tgattgagtc     900
cctatcaaca aattcagtgt acttagacaa cagtgcttct gattcaaatc aagtggtgga     960
ctacaaggac tggcagataa ccttgagcag aagatttcgt gcactcaaag tttggcttgt    1020
tctgagaagc tatggtgttg ctaatctaag aaacttcctc agaagccacg ttgaaatggc    1080
caagagtttt gaagagttgg tgagaaagga caagagggtt gagattttg tgcctaggaa    1140
tcttgctgtg gtttgcttca ggcttttacc ttctgcagtt gcaaggattg gtaatggcag    1200
ggtccaaaat ggagatgtta caactgaggg tgttgcaaat gaaatcaacc gcaaattgct    1260
ggattccatc aatggttcag gattagtgta catgactcat gcaaatgttg gagggttttt    1320
cgtgattagg tgtgccatag gagcaacttt aactgagaaa acgcatgtaa tcatggcctg    1380
gaaggtggtt caggaacatg cagatgcaat tctaaatcat taagttaaat ctgaatttga    1440
cagaaaaaaa tgagtttttc tttatctttt tattttttt atcagtagag tccaattgtt    1500
cagaaactgt attggttacc gtggttgcaa aattaaattt gttttcaaag tgttttcatg    1560
gtc                                                                1563
```

<210> SEQ ID NO 12
<211> LENGTH: 473
<212> TYPE: PRT
<213> ORGANISM: Glycine max

<400> SEQUENCE: 12

```
His Glu Asn Ile Ala Asn Tyr Pro Val Leu Ser Gln Val Glu Pro Gly
  1               5                  10                  15

Tyr Leu Arg Glu Leu Met Pro Tyr Phe Ala Pro Leu Asn Pro Glu Pro
             20                  25                  30

Ile Glu Thr Ile Leu Gln Asp Leu Gln Gln His Ile Val Pro Gly Ile
         35                  40                  45
```

-continued

```
Thr His Trp Gln Ser Pro Asn Tyr Phe Ala Tyr Phe Pro Ser Ser Gly
 50                  55                  60

Ser Thr Ala Gly Phe Leu Gly Glu Met Leu Ser Thr Gly Phe Asn Leu
 65                  70                  75                  80

Val Gly Phe Asn Trp Val Ser Pro Ala Ala Thr Glu Leu Glu Ser
                     85                  90                  95

Thr Val Met Asp Trp Leu Gly Gln Val Leu Lys Leu Pro Lys Ala Phe
                100                 105                 110

Leu Phe Ser Gly Ser Gly Gly Val Leu Leu Gly Thr Thr Cys Glu
                115                 120                 125

Ala Ile Leu Val Thr Leu Val Ala Ala Arg Asp Lys Val Leu Gly Gln
130                 135                 140

Ile Gly Arg Glu Asn Ile Cys Lys Leu Val Val Tyr Val Ser Asp Gln
145                 150                 155                 160

Thr His Cys Ala Val Gln Lys Ala Ala His Ile Ile Gly Ile His His
                165                 170                 175

Lys Asn Ile Arg Ala Val Lys Thr Met Lys Ser Thr Ser Phe Thr Leu
                180                 185                 190

Leu Pro Glu Ser Leu Leu Ser Ala Ile His Thr Asp Val Gln Asn Gly
                195                 200                 205

Leu Val Pro Cys Tyr Leu Cys Ala Thr Val Gly Thr Thr Ser Thr Thr
210                 215                 220

Ala Val Asp Pro Leu Gly Pro Leu Cys Lys Val Ala Lys Glu Tyr Gly
225                 230                 235                 240

Met Trp Val His Val Asp Ala Ala Tyr Ala Gly Ser Ala Cys Ile Cys
                245                 250                 255

Pro Glu Phe Arg His Leu Ile Asp Gly Val Glu Gly Ala Asn Ser Phe
                260                 265                 270

Ser Leu Asn Ala His Lys Trp Phe Leu Thr Asn Leu Asp Cys Cys Cys
                275                 280                 285

Leu Trp Leu Lys Asp Pro Ala Ser Val Ile Glu Ser Leu Ser Thr Asn
                290                 295                 300

Ser Val Tyr Leu Asp Asn Ser Ala Ser Asp Ser Asn Gln Val Val Asp
305                 310                 315                 320

Tyr Lys Asp Trp Gln Ile Thr Leu Ser Arg Arg Phe Arg Ala Leu Lys
                325                 330                 335

Val Trp Leu Val Leu Arg Ser Tyr Gly Val Ala Asn Leu Arg Asn Phe
                340                 345                 350

Leu Arg Ser His Val Glu Met Ala Lys Ser Phe Glu Glu Leu Val Arg
                355                 360                 365

Lys Asp Lys Arg Phe Glu Ile Phe Val Pro Arg Asn Leu Ala Val Val
                370                 375                 380

Cys Phe Arg Leu Leu Pro Ser Ala Val Ala Arg Ile Gly Asn Gly Arg
385                 390                 395                 400

Val Gln Asn Gly Asp Val Thr Thr Glu Gly Val Ala Asn Glu Ile Asn
                405                 410                 415

Arg Lys Leu Leu Asp Ser Ile Asn Gly Ser Gly Leu Val Tyr Met Thr
                420                 425                 430

His Ala Asn Val Gly Gly Val Phe Val Ile Arg Cys Ala Ile Gly Ala
                435                 440                 445

Thr Leu Thr Glu Lys Thr His Val Ile Met Ala Trp Lys Val Val Gln
                450                 455                 460
```

Glu His Ala Asp Ala Ile Leu Asn His
465                 470

<210> SEQ ID NO 13
<211> LENGTH: 1459
<212> TYPE: DNA
<213> ORGANISM: Triticum aestivum

<400> SEQUENCE: 13

| | | | | | |
|---|---|---|---|---|---|
| ctggattcct | gggggagatg | cttagtgctg | cctttaacat | cgttggcttc | agttggataa | 60 |
| cctctcctgc | tgcaactgag | ctagaggtta | tagtcttaga | ctggtttgca | aaaatgctta | 120 |
| agcttccaag | ccaatttctg | tcagatgcgc | ctggtggagg | agtaatccag | ggtactgcca | 180 |
| gtgaagcagt | tcttgttgta | ctattggctg | cacgagatag | aactttaaag | aagcatggga | 240 |
| aaaagtccct | tgaaaagtta | gtagtttatg | catctgatca | gacacattct | gctctgcaaa | 300 |
| aggcatgcca | gattgcagga | attttcccag | agaacttcag | agttgtcaaa | gctgactgta | 360 |
| gtaagaacta | tgctgttgca | cctgaagcag | tgacagaggc | catttccatt | gacttgtcat | 420 |
| ctggtttgat | accattcttc | atctgtgcaa | cagtaggcac | aacatcttca | tcggccgtgg | 480 |
| accccttgcc | tgaactagga | aacatagcac | agggccatga | catgtggttc | cacattgatg | 540 |
| ctgcatatgc | tggaagtgct | tgtatatgcc | cagagtatcg | acatcacctt | gatggagtgg | 600 |
| aaaaagctga | ttcattcaat | atgaatgcac | acaaatggtt | cctcacaaac | ttcgactgtt | 660 |
| ctttgctatg | ggttaaggac | aggagttatc | ttgtggaagc | attgtctaca | aatccagagt | 720 |
| ttcttaagaa | taaggcttcc | caagcaaatt | ctgttgttga | tttcaaggat | tggcaaattc | 780 |
| cacttggtcg | tcgttttaga | tcactcaagc | tatggatggt | ctcgaggctt | atggcgtgg | 840 |
| aaaatctgca | gagttatatc | agaaagcaca | tacagttggc | tgaacatttt | gaacaacttg | 900 |
| tactatctga | ctcaagattt | gaggttgtga | ctccgagact | tttttccctt | gtttgtttcc | 960 |
| gccttctgcc | cccaactttt | gaggatgagg | gtggtcgtca | acttaactat | gacctaatgg | 1020 |
| atgccgctaa | ctcaagtggg | aagatcttca | tctcacatac | ggttcttgct | ggcaagtttg | 1080 |
| tcttgagatt | tgcggttgga | gcaccgctga | cagaggagca | acatgtggat | gccgcttgga | 1140 |
| agctcttgca | agatgaggcc | accaagctct | caggaagtgc | gtaggttact | ataatggcaa | 1200 |
| tgttcattg | attaagctgc | agtgttcagg | cctattatca | tgataagctt | tcacagctgc | 1260 |
| tcatacaaac | agttttttgaa | agaaacttgg | acagttgaaa | tacgaaacta | ctatatccat | 1320 |
| acgatctttc | ctcgtcatgt | taaatcgaat | gcttactgaa | ctttcattcc | atgcgccaac | 1380 |
| ggcttgattt | ggcgtattgg | atgggaatca | gacaatcctt | gaacaaatag | aataacaaat | 1440 |
| tgtgtgcatt | ntgtntaaa | | | | | 1459 |

<210> SEQ ID NO 14
<211> LENGTH: 393
<212> TYPE: PRT
<213> ORGANISM: Triticum aestivum

<400> SEQUENCE: 14

Gly Phe Leu Gly Glu Met Leu Ser Ala Ala Phe Asn Ile Val Gly Phe
1               5                   10                  15

Ser Trp Ile Thr Ser Pro Ala Ala Thr Glu Leu Glu Val Ile Val Leu
            20                  25                  30

Asp Trp Phe Ala Lys Met Leu Lys Leu Pro Ser Gln Phe Leu Ser Asp
        35                  40                  45

Ala Pro Gly Gly Gly Val Ile Gln Gly Thr Ala Ser Glu Ala Val Leu

```
                50                  55                  60
Val Val Leu Ala Ala Arg Asp Arg Thr Leu Lys Lys His Gly Lys
 65                  70                  75                  80

Lys Ser Leu Glu Lys Leu Val Val Tyr Ala Ser Asp Gln Thr His Ser
                 85                  90                  95

Ala Leu Gln Lys Ala Cys Gln Ile Ala Gly Ile Phe Pro Glu Asn Phe
                100                 105                 110

Arg Val Val Lys Ala Asp Cys Ser Lys Asn Tyr Ala Val Ala Pro Glu
                115                 120                 125

Ala Val Thr Glu Ala Ile Ser Ile Asp Leu Ser Ser Gly Leu Ile Pro
                130                 135                 140

Phe Phe Ile Cys Ala Thr Val Gly Thr Thr Ser Ser Ser Ala Val Asp
145                 150                 155                 160

Pro Leu Pro Glu Leu Gly Asn Ile Ala Gln Gly His Asp Met Trp Phe
                165                 170                 175

His Ile Asp Ala Ala Tyr Ala Gly Ser Ala Cys Ile Cys Pro Glu Tyr
                180                 185                 190

Arg His His Leu Asp Gly Val Glu Lys Ala Asp Ser Phe Asn Met Asn
                195                 200                 205

Ala His Lys Trp Phe Leu Thr Asn Phe Asp Cys Ser Leu Leu Trp Val
210                 215                 220

Lys Asp Arg Ser Tyr Leu Val Glu Ala Leu Ser Thr Asn Pro Glu Phe
225                 230                 235                 240

Leu Lys Asn Lys Ala Ser Gln Ala Asn Ser Val Val Asp Phe Lys Asp
                245                 250                 255

Trp Gln Ile Pro Leu Gly Arg Arg Phe Arg Ser Leu Lys Leu Trp Met
                260                 265                 270

Val Ser Arg Leu Tyr Gly Val Glu Asn Leu Gln Ser Tyr Ile Arg Lys
                275                 280                 285

His Ile Gln Leu Ala Glu His Phe Glu Gln Leu Val Leu Ser Asp Ser
                290                 295                 300

Arg Phe Glu Val Val Thr Pro Arg Leu Phe Ser Leu Val Cys Phe Arg
305                 310                 315                 320

Leu Leu Pro Pro Thr Phe Glu Asp Glu Gly Gly Arg Gln Leu Asn Tyr
                325                 330                 335

Asp Leu Met Asp Ala Ala Asn Ser Ser Gly Lys Ile Phe Ile Ser His
                340                 345                 350

Thr Val Leu Ala Gly Lys Phe Val Leu Arg Phe Ala Val Gly Ala Pro
                355                 360                 365

Leu Thr Glu Glu Gln His Val Asp Ala Ala Trp Lys Leu Leu Gln Asp
                370                 375                 380

Glu Ala Thr Lys Leu Ser Gly Ser Ala
385                 390
```

<210> SEQ ID NO 15
<211> LENGTH: 915
<212> TYPE: DNA
<213> ORGANISM: Zea mays

<400> SEQUENCE: 15

```
ccacgcgtcc gcgccgccgt gttcaacgcc tgggtccaca tcgacgccgc ctacgccggc      60
agcgcgtgca tctgcccgga gttccggcac cacctggacg gcgtggagcg cgtggactcc     120
atcagcatga gcccgcacaa gtggctcatg acgtgcctgg attgcacgtg cttgtgggtg     180
```

-continued

```
cgggacacgc accggctcac cgattctctc gaaaccaacc cggagtacct caagaacgac      240
gccagcgagt ccggcaccgt caccgacctc aaggacatgc aggtcggcgt cggccgccgc      300
ttccgcgggc tcaagctctg gatggtcatg cgcacctacg gctccgccaa gctccaggag      360
cacatccgga gcgacgtcgc catggccaag atgttcgagg acgccgtgcg tgccgaccac      420
cgcttcgaga tcgtggtgcc gaggaacttc gcgctcgtgt gcttcaggat caggccacag      480
ggcaccgcca tgacggagga ggacgccgac gtggtcaacc gtgagctaat ggagcgcctg      540
aacaggacgg gcaaggcgta cctggcgcat acgcgatcg gcggcaagtt cgtgctgcgg       600
ttcgcggtgg ggtcgtcgct gcaggaagag aggcacgtgc gaagcgcgtg ggagctcatc      660
aagaagacga ccaccgagat cttcgaggaa gagacgatgt agagagtata ttactataga      720
ttatcgtcat tcttatttat tgattgatgc agctggacta ataaatatgg ttatgcatga      780
caatcgaaag gtgacgtcca ataaagcctt tcgtgatgca tatatattca tgcaagaaat      840
ttatgtatgt tggacttgga gtatatatac atgactgcca tgtattattt atatatatgg      900
gctataataa taaaa                                                       915
```

<210> SEQ ID NO 16
<211> LENGTH: 223
<212> TYPE: PRT
<213> ORGANISM: Zea mays

<400> SEQUENCE: 16

```
Phe Asn Ala Trp Val His Ile Asp Ala Ala Tyr Ala Gly Ser Ala Cys
  1               5                  10                  15

Ile Cys Pro Glu Phe Arg His His Leu Asp Gly Val Glu Arg Val Asp
             20                  25                  30

Ser Ile Ser Met Ser Pro His Lys Trp Leu Met Thr Cys Leu Asp Cys
         35                  40                  45

Thr Cys Leu Trp Val Arg Asp Thr His Arg Leu Thr Asp Ser Leu Glu
     50                  55                  60

Thr Asn Pro Glu Tyr Leu Lys Asn Asp Ala Ser Glu Ser Gly Thr Val
 65                  70                  75                  80

Thr Asp Leu Lys Asp Met Gln Val Gly Val Gly Arg Arg Phe Arg Gly
                 85                  90                  95

Leu Lys Leu Trp Met Val Met Arg Thr Tyr Gly Ser Ala Lys Leu Gln
            100                 105                 110

Glu His Ile Arg Ser Asp Val Ala Met Ala Lys Met Phe Glu Asp Ala
        115                 120                 125

Val Arg Ala Asp His Arg Phe Glu Ile Val Val Pro Arg Asn Phe Ala
    130                 135                 140

Leu Val Cys Phe Arg Ile Arg Pro Gln Gly Thr Ala Met Thr Glu Glu
145                 150                 155                 160

Asp Ala Asp Val Val Asn Arg Glu Leu Met Glu Arg Leu Asn Arg Thr
                165                 170                 175

Gly Lys Ala Tyr Leu Ala His Thr Ala Ile Gly Gly Lys Phe Val Leu
            180                 185                 190

Arg Phe Ala Val Gly Ser Ser Leu Gln Glu Glu Arg His Val Arg Ser
        195                 200                 205

Ala Trp Glu Leu Ile Lys Lys Thr Thr Thr Glu Ile Phe Glu Glu
    210                 215                 220
```

<210> SEQ ID NO 17
<211> LENGTH: 1377

<212> TYPE: DNA
<213> ORGANISM: Oryza sativa

<400> SEQUENCE: 17

| | | | | | |
|---|---|---|---|---|---|
| gcacgagtac | agcccgccgc | gatcgccggt | gagctcatcg | cgtcggcgat | gaacaccgtc | 60 |
| ggattcacgt | ggcaggcggc | gccggcggcg | accgagctgg | aggtgctcgc | gctggattgg | 120 |
| ctcgcgcagc | tgctcgggtt | gccggcgagt | ttcatgaacc | gcaccgtcgc | cggtgggcgc | 180 |
| ggcaccggcg | ggggcgtcat | tctggggacc | accagcgagg | cgatgctcgt | cacgctcgtc | 240 |
| gccgcgcgcg | acgccgcgct | cgcggcggagc | gggtccaatg | gcgtggcggg | catcacgcgg | 300 |
| ctgacggtgt | acgccgccga | ccagacgcac | tccacgttct | tcaaggcgag | gctgctggag | 360 |
| gcgatgcagg | ccgacgccga | cgccgggctg | gtgcccacct | acgtgtgcgc | cacggtggga | 420 |
| accacgtcgt | ccaacgccgt | cgacccggtg | ggcgccgtgg | ccgacgtcgc | ggcgaggttc | 480 |
| gcggcgtggg | tgcacgtcga | cgcggcgtac | gccggcagcg | cgtgcatctg | cccggagttc | 540 |
| cggcaccacc | tcgacggcgt | ggagcgtgtc | gactccatca | gcatgagccc | ccacaagtgg | 600 |
| ctgatgacct | gcctcgactg | cacctgcctc | tacgtccgcg | acacccaccg | cctcaccggc | 660 |
| tccctcgaga | ccaacccgga | gtacctcaag | aaccacgcca | gcgactccgg | cgaggtcacc | 720 |
| gacctcaagg | acatgcaggt | cggcgtcggc | cgccgcttcc | gggggctcaa | gctctggatg | 780 |
| gtcatgcgca | cctacggcgc | cggcaagctg | caggagcaca | tccggagcga | cgtcgccatg | 840 |
| gccaagacgt | tcgaggacct | cgtccgcggc | gacgaccggt | tcgaggtcgt | ggtgccgagg | 900 |
| aacttcgcgc | tcgtctgctt | caggatcagg | ccgaggaaat | ccggcgccgc | catcgccgcc | 960 |
| ggcgaggcgg | aggccgagaa | ggcgaaccgc | gagctgatgg | agcggctgaa | caagaccgga | 1020 |
| aaggcttacg | tggcgcacac | ggtggtcggc | ggcaggttcg | tgctgcgctt | cgcggtgggg | 1080 |
| tcgtcgctgc | aggaggagcg | gcacgtgcga | agcgcgtggg | agctcatcaa | gaagacgacc | 1140 |
| accgagatcg | tcgccgacgc | cggagaagac | aagtagatcg | agctcgacgg | cgacagtgta | 1200 |
| aagccactgt | tatttgctgt | gtcgtgtccg | ttcgatacat | ggattgatta | attgtttact | 1260 |
| ggtcgcagtt | ggtagaagta | attaatggcg | acaacgagag | gtgcgtggaa | taataaatac | 1320 |
| tctctccacg | taggcagtgt | gtgtgtgtga | ttatattcat | actgtgcatt | caaaatt | 1377 |

<210> SEQ ID NO 18
<211> LENGTH: 391
<212> TYPE: PRT
<213> ORGANISM: Oryza sativa

<400> SEQUENCE: 18

Ala Arg Val Gln Pro Ala Ala Ile Ala Gly Glu Leu Ile Ala Ser Ala
 1               5                  10                  15

Met Asn Thr Val Gly Phe Thr Trp Gln Ala Ala Pro Ala Ala Thr Glu
             20                  25                  30

Leu Glu Val Leu Ala Leu Asp Trp Leu Ala Gln Leu Leu Gly Leu Pro
         35                  40                  45

Ala Ser Phe Met Asn Arg Thr Val Ala Gly Arg Gly Thr Gly Gly
     50                  55                  60

Gly Val Ile Leu Gly Thr Thr Ser Glu Ala Met Leu Val Thr Leu Val
 65                  70                  75                  80

Ala Ala Arg Asp Ala Ala Leu Arg Arg Ser Gly Ser Asn Gly Val Ala
                 85                  90                  95

Gly Ile Thr Arg Leu Thr Val Tyr Ala Ala Asp Gln Thr His Ser Thr
            100                 105                 110

-continued

```
Phe Phe Lys Ala Arg Leu Leu Glu Ala Met Gln Ala Asp Ala Asp Ala
        115                 120                 125
Gly Leu Val Pro Thr Tyr Val Cys Ala Thr Val Gly Thr Thr Ser Ser
    130                 135                 140
Asn Ala Val Asp Pro Val Gly Ala Val Ala Asp Val Ala Ala Arg Phe
145                 150                 155                 160
Ala Ala Trp Val His Val Asp Ala Ala Tyr Ala Gly Ser Ala Cys Ile
                165                 170                 175
Cys Pro Glu Phe Arg His His Leu Asp Gly Val Glu Arg Val Asp Ser
            180                 185                 190
Ile Ser Met Ser Pro His Lys Trp Leu Met Thr Cys Leu Asp Cys Thr
        195                 200                 205
Cys Leu Tyr Val Arg Asp Thr His Arg Leu Thr Gly Ser Leu Glu Thr
    210                 215                 220
Asn Pro Glu Tyr Leu Lys Asn His Ala Ser Asp Ser Gly Glu Val Thr
225                 230                 235                 240
Asp Leu Lys Asp Met Gln Val Gly Val Gly Arg Arg Phe Arg Gly Leu
                245                 250                 255
Lys Leu Trp Met Val Met Arg Thr Tyr Gly Ala Gly Lys Leu Gln Glu
            260                 265                 270
His Ile Arg Ser Asp Val Ala Met Ala Lys Thr Phe Glu Asp Leu Val
        275                 280                 285
Arg Gly Asp Asp Arg Phe Glu Val Val Pro Arg Asn Phe Ala Leu
    290                 295                 300
Val Cys Phe Arg Ile Arg Pro Arg Lys Ser Gly Ala Ala Ile Ala Ala
305                 310                 315                 320
Gly Glu Ala Glu Ala Glu Lys Ala Asn Arg Glu Leu Met Glu Arg Leu
                325                 330                 335
Asn Lys Thr Gly Lys Ala Tyr Val Ala His Thr Val Val Gly Gly Arg
            340                 345                 350
Phe Val Leu Arg Phe Ala Val Gly Ser Ser Leu Gln Glu Glu Arg His
        355                 360                 365
Val Arg Ser Ala Trp Glu Leu Ile Lys Lys Thr Thr Thr Glu Ile Val
    370                 375                 380
Ala Asp Ala Gly Glu Asp Lys
385                 390
```

<210> SEQ ID NO 19
<211> LENGTH: 1944
<212> TYPE: DNA
<213> ORGANISM: Triticum aestivum

<400> SEQUENCE: 19

| | | | | | |
|---|---|---|---|---|---|
| gcacgagact | agctcctccg | cctcttcttc | ttgctctccg | gcagcaaagc | tacctagctc | 60 |
| aacttcatta | agccaatcct | tctctccgcc | tcccaacctt | ctttgctcat | aatcaaggtt | 120 |
| taaattacct | acctaaaagg | aatgggcagc | ttgggcacca | accccatgtc | cttctccgcc | 180 |
| atccccgacg | acaaggcggc | gttcgagccg | ctcaaccccg | aagatgtccg | tgcataccgc | 240 |
| cacaaggccg | ttgacttcat | ctccgactac | tacaccaaca | tcgagtccat | gcccgtactc | 300 |
| cctaacgtga | agccggggta | cctgcaagac | gagctcagcg | catccccgcc | aacttactct | 360 |
| gcgccattcg | acgtcaccat | gaaggagctc | aggacctccg | ttgtcccggg | catgacgcac | 420 |
| tgggctagcc | ccaacttctt | cgccttcttc | ccctccacca | acagcgcagc | tgcgatcgcc | 480 |

-continued

```
ggcgacctca ttgcctcagc catgaacacc gtcggattca cgtggcaggc ctcacctgcc    540
gccactgaga tggaggttct cgctctcgac tggcttgcgc agctcctgcg tctgcccaca    600
accttcatga accgcaccag cactggtcgt ggcaccggtg gtggggttat ccttggcaca    660
acaagcgagg ccatgctcgt cacgctagtc gccgcccgtg atgcagcgct cgtcgaagc    720
ggctctgtcg gcgtgtctgg cattccacgc ttggctgtgt atgctgccga ccaaacccac    780
tccacgttct tcaaggcttg tcgcctcgcg ggatttgacc ccgccaacat ccgctccatc    840
cctaccgggc cagaaaccaa ttatgggctc gacccggcaa agcttctcga ggtcatgcaa    900
gctgatgccg acgctggtct tgtgccaaca tatgtctgcg caaccgtggg caccacgtct    960
tccaatgtct tgacccggt gggcgacgtc gccgatgttg ccgccatgtt cagtgcatgg    1020
gtccacgtcg atgctgccta cgctggcagt gcatgtatct gccctgagtt tcgccaccat   1080
ctcgacggcg tcgagcgcgt ggactccatt agcatgagcc cacacaaatg cttctcaca   1140
tgccttgatt gcacatgtct ctatgtccgt gatgctcacc gactgagtga ctcattggag   1200
accaacccgg agtatctcaa gaatgatgct accgagtccg gcgaggtcac cgatcttaaa   1260
gacatgcagg tcggcgttgg ccggcgcttc cgcgggctca agctttggat ggtcatgcgt   1320
acctatggta ccgcaaagct ccaagagcac atccgtagtg atgttgccat ggccaagatg   1380
tttgaagatt tcgtccgtgc cgatgacagg tttgaagtgg tcgtaccgag gaactttgct   1440
cttgtttgct ttcggatcaa ggcaagtgga gccatgacgg agaaggatgc tgacgaggcc   1500
aaccgcgtgc taatggaaaa tctgaacaaa actggcaagg cttatcttgc acacacggtg   1560
atcggtgaca aatttgtgct ccgtttcgcc gttggatcgt cgctgcaaga ggaaaggcat   1620
gtgagaagtg catgggacct catcaagaag accacgagca gtatcatgga ttaagtgcat   1680
ggacctactg ttcaagaagc taaacaaatt cctatattta gggtacaatt attattttac   1740
atttcttgtt cttttattct cctttgatta tgattattat tattgttatt tatttagaca   1800
tggggttctt attcctttt tgatctatat ataccgaccg agggtctata tatatagcag   1860
gccggtacca aagaaattgg ttgtacactg taaaagggct tatacttaat atacatgata   1920
tgatttttt tttgttaaaa aaaa                                          1944
```

<210> SEQ ID NO 20
<211> LENGTH: 509
<212> TYPE: PRT
<213> ORGANISM: Triticum aestivum

<400> SEQUENCE: 20

Met Gly Ser Leu Gly Thr Asn Pro Met Ser Phe Ser Ala Ile Pro Asp
1               5                   10                  15

Asp Lys Ala Ala Phe Glu Pro Leu Asn Pro Glu Asp Val Arg Ala Tyr
            20                  25                  30

Leu His Lys Ala Val Asp Phe Ile Ser Asp Tyr Tyr Thr Asn Ile Glu
        35                  40                  45

Ser Met Pro Val Leu Pro Asn Val Lys Pro Gly Tyr Leu Gln Asp Glu
    50                  55                  60

Leu Ser Ala Ser Pro Pro Thr Tyr Ser Ala Pro Phe Asp Val Thr Met
65                  70                  75                  80

Lys Glu Leu Arg Thr Ser Val Val Pro Gly Met Thr His Trp Ala Ser
                85                  90                  95

Pro Asn Phe Phe Ala Phe Pro Ser Thr Asn Ser Ala Ala Ala Ile
            100                 105                 110

```
Ala Gly Asp Leu Ile Ala Ser Ala Met Asn Thr Val Gly Phe Thr Trp
        115                 120                 125

Gln Ala Ser Pro Ala Ala Thr Glu Met Glu Val Leu Ala Leu Asp Trp
130                 135                 140

Leu Ala Gln Leu Leu Arg Leu Pro Thr Thr Phe Met Asn Arg Thr Ser
145                 150                 155                 160

Thr Gly Arg Gly Thr Gly Gly Val Ile Leu Gly Thr Thr Ser Glu
                165                 170                 175

Ala Met Leu Val Thr Leu Val Ala Ala Arg Asp Ala Ala Leu Arg Arg
                180                 185                 190

Ser Gly Ser Val Gly Val Ser Gly Ile Pro Arg Leu Ala Val Tyr Ala
                195                 200                 205

Ala Asp Gln Thr His Ser Thr Phe Phe Lys Ala Cys Arg Leu Ala Gly
        210                 215                 220

Phe Asp Pro Ala Asn Ile Arg Ser Ile Pro Thr Gly Pro Glu Thr Asn
225                 230                 235                 240

Tyr Gly Leu Asp Pro Ala Lys Leu Leu Glu Val Met Gln Ala Asp Ala
                245                 250                 255

Asp Ala Gly Leu Val Pro Thr Tyr Val Cys Ala Thr Val Gly Thr Thr
                260                 265                 270

Ser Ser Asn Val Val Asp Pro Val Gly Asp Val Ala Asp Val Ala Ala
                275                 280                 285

Met Phe Ser Ala Trp Val His Val Asp Ala Ala Tyr Ala Gly Ser Ala
        290                 295                 300

Cys Ile Cys Pro Glu Phe Arg His His Leu Asp Gly Val Glu Arg Val
305                 310                 315                 320

Asp Ser Ile Ser Met Ser Pro His Lys Trp Leu Leu Thr Cys Leu Asp
                325                 330                 335

Cys Thr Cys Leu Tyr Val Arg Asp Ala His Arg Leu Ser Asp Ser Leu
                340                 345                 350

Glu Thr Asn Pro Glu Tyr Leu Lys Asn Asp Ala Thr Glu Ser Gly Glu
                355                 360                 365

Val Thr Asp Leu Lys Asp Met Gln Val Gly Val Gly Arg Arg Phe Arg
        370                 375                 380

Gly Leu Lys Leu Trp Met Val Met Arg Thr Tyr Gly Thr Ala Lys Leu
385                 390                 395                 400

Gln Glu His Ile Arg Ser Asp Val Ala Met Ala Lys Met Phe Glu Asp
                405                 410                 415

Phe Val Arg Ala Asp Asp Arg Phe Glu Val Val Val Pro Arg Asn Phe
                420                 425                 430

Ala Leu Val Cys Phe Arg Ile Lys Ala Ser Gly Ala Met Thr Glu Lys
        435                 440                 445

Asp Ala Asp Glu Ala Asn Arg Val Leu Met Glu Asn Leu Asn Lys Thr
450                 455                 460

Gly Lys Ala Tyr Leu Ala His Thr Val Ile Gly Asp Lys Phe Val Leu
465                 470                 475                 480

Arg Phe Ala Val Gly Ser Ser Leu Gln Glu Glu Arg His Val Arg Ser
                485                 490                 495

Ala Trp Asp Leu Ile Lys Lys Thr Thr Ser Ser Ile Met
                500                 505
```

AMINO ACID DECARBOXYLASES

This application claims priority benefit of U.S. Provisional Application No. 60/099,493 filed Sep. 8, 1998, now abandoned.

FIELD OF THE INVENTION

This invention is in the field of plant molecular biology. More specifically, this invention pertains to nucleic acid fragments encoding amino acid decarboxylases in plants and seeds.

BACKGROUND OF THE INVENTION

In addition to their role as protein monomeric units, amino acids are energy metabolites and precursors of many biologically important nitrogen-containing compounds, such as heme, physiologically active amines, glutathione, other amino acids, nucleotides, and nucleotide coenzymes. Excess dietary amino acids are neither stored for future use nor excreted. Rather they are converted to common metabolic intermediates such as pyruvate, oxaloacetate and alpha-ketoglutarate. Consequently, amino acids are also precursors of glucose, fatty acids and ketone bodies and are therefore metabolic fuels.

Amino acid decarboxylases are induced in cells as a response to various forms of stress. In *Salmonella typhimurium* lysine decarboxylase (EC 4.1.1.18) is induced by low pH, is required for acid tolerance, and contributes significantly to pH homeostasis in environments as low as pH 3.0 (Park et al. (1996) *Mol. Microbiol.* 20:605–611). At least two different lysine decarboxylases exist in *Escherichia coli*: an extensively characterized inducible decarboxylase, and a decarboxylase which is present in low amounts upon derepression by an as yet undetermined factor (Lemonnier and Lane (1998) *Microbiology* 144:751–760). A monomeric lysine decarboxylase from soybean has been purified and characterized, but its sequence has not yet been determined (Kim et al. (1998) *Arch. Biochem. Biophys.* 354:40–46).

Two similar but distinct enzymes are referred to as dopa decarboxylase:tyrosine decarboxylase and tryptophan decarboxylase. Dopa decarboxylase:tyrosine decarboxylase has been shown to be involved in several different pathways such as histidine metabolism, tyrosine metabolism, tryptophan metabolism, phenylalanine metabolism, and alkaloid biosynthesis. In the eastern tiger swallowtail butterfly *Papilio glaucus* dopa decarboxylase:tyrosine decarboxylase provides dopamine to the two major color pigments, papiliochrome (yellow) and melanin (black). Dopa decarboxylase:tyrosine decarboxylase activity is spatially and temporally regulated, being utilized early in presumptive yellow tissues and later in black, forming part of a developmental switch between yellow or black (Koch et al. (1998) *Development* 125:2303–2313).

L-tyrosine decarboxylase (EC 4.1.1.25) is involved in an early, and potential rate-limiting step, in the biosynthesis of isoquinoline alkaloids, such as morphine and codeine, in opium poppy (*Papaver somniferum*). This enzyme catalyzes the conversion of L-tyrosine to tyramine and carbon dioxide. Several members of the tyrosine decarboxylase family, differentially expressed in various tissues, have been identified in poppy (Facchini and De Luca (1994) *J. Biol. Chem.* 269:26684–26690). Four parsley (*Petroselinum crispum*) tyrosine decarboxylases have been identified from cDNAs representing genes that are transcriptionally activated upon fungal infection or elicitor treatment. The deduced protein sequences share extensive similarity with two functionally related enzymes, tryptophan decarboxylase from periwinkle and dopa decarboxylase:tyrosine decarboxylase from *Drosophila melanogaster* (Kawalleck et al. (1993) *J. Biol. Chem.* 268:2189–2194).

Tryptophan decarboxylase (EC 4.1.1.28) catalyzes a key step in the biosynthesis of terpenoid indole alkaloids catalyzing the conversion of tryptophan to tryptamine and carbon dioxide. Chimeric gene constructs in which a tryptophan decarboxylase cDNA is linked in the sense or antisense orientation to the cauliflower mosaic virus 35S promoter and terminator have been expressed in callus and cell suspension cultures. Calluses harboring the tryptophan decarboxylase sense construct showed increased levels of tryptophan decarboxylase protein and activity, as well as the tryptamine content, but no significant increase in terpenoid indole alkaloid (Goddijn et al. (1995) *Transgenic Res.* 4:315–323). Tryptophan decarboxylase supplies tryptamine for the indole moiety of Camptothecin, a valuable anticancer monoterpene alkaloid, and its derivatives. Tryptophan decarboxylase is considered a key step in monoterpene indole alkaloid biosynthesis as it links primary and secondary metabolism. Two autonomously regulated tryptophan decarboxylase genes from Camptotheca have been identified and isolated. One of these genes is part of a developmentally regulated chemical defense system while the other gene serves as part of a defense system induced during pathogen challenge. When expressed in *Escherichia coli*, the product of each gene will decarboxylate tryptophan, but is inactive against tyrosine, phenylalanine and 3,4-dihydroxyphenylalanine (dopa) (Lopez-Meyer and Nessler (1997) *Plant J.* 11:1167–1175).

SUMMARY OF THE INVENTION

The instant invention relates to isolated nucleic acid fragments encoding amino acid decarboxylases. Specifically, this invention concerns an isolated nucleic acid fragment encoding a lysine decarboxylase, a tyrosine decarboxylase or a tryptophan decarboxylase and an isolated nucleic acid fragment that is substantially similar to an isolated nucleic acid fragment encoding a lysine decarboxylase, a tyrosine decarboxylase or a tryptophan decarboxylase. In addition, this invention relates to a nucleic acid fragment that is complementary to the nucleic acid fragment encoding lysine decarboxylase, tyrosine decarboxylase or tryptophan decarboxylase.

An additional embodiment of the instant invention pertains to a polypeptide encoding all or a substantial portion of an amino acid decarboxylase selected from the group consisting of lysine decarboxylase, tyrosine decarboxylase and tryptophan decarboxylase.

In another embodiment, the instant invention relates to a chimeric gene encoding a lysine decarboxylase, a tyrosine decarboxylase or a tryptophan decarboxylase, or to a chimeric gene that comprises a nucleic acid fragment that is complementary to a nucleic acid fragment encoding a lysine decarboxylase, a tyrosine decarboxylase or a tryptophan decarboxylase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a lysine decarboxylase, a tyrosine decarboxylase or a tryptophan decarboxylase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a lysine decarboxylase, a tyrosine decarboxylase or a tryptophan decarboxylase in a transformed host cell comprising: a) transforming a host cell with a chimeric gene comprising a nucleic acid fragment encoding a lysine decarboxylase, a tyrosine decarboxylase or a tryptophan decarboxylase; and b) growing the transformed host cell under conditions that are suitable for expression of the chimeric gene wherein expression of the chimeric gene results in production of altered levels of lysine decarboxylase, tyrosine decarboxylase or tryptophan decarboxylase in the transformed host cell.

An addition embodiment of the instant invention concerns a method for obtaining a nucleic acid fragment encoding all or a substantial portion of an amino acid sequence encoding a lysine decarboxylase, a tyrosine decarboxylase or a tryptophan decarboxylase.

A further embodiment of the instant invention is a method for evaluating at least one compound for its ability to inhibit the activity of a lysine decarboxylase, a tyrosine decarboxylase or a tryptophan decarboxylase, the method comprising the steps of: (a) transforming a host cell with a chimeric gene comprising a nucleic acid fragment encoding a lysine decarboxylase, a tyrosine decarboxylase or a tryptophan decarboxylase, operably linked to suitable regulatory sequences; (b) growing the transformed host cell under conditions that are suitable for expression of the chimeric gene wherein expression of the chimeric gene results in production of lysine decarboxylase, tyrosine decarboxylase or tryptophan decarboxylase in the transformed host cell; (c) optionally purifying the lysine decarboxylase, the tyrosine decarboxylase or the tryptophan decarboxylase expressed by the transformed host cell; (d) treating the lysine decarboxylase, the tyrosine decarboxylase or the tryptophan decarboxylase with a compound to be tested; and (e) comparing the activity of the lysine decarboxylase, the tyrosine decarboxylase or the tryptophan decarboxylase that has been treated with a test compound to the activity of an untreated lysine decarboxylase, tyrosine decarboxylase or tryptophan decarboxylase, thereby selecting compounds with potential for inhibitory activity.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. § 1.821–1.825.

TABLE 1

Amino Acid Decarboxylases

| | | SEQ ID NO: | |
|---|---|---|---|
| Protein | Clone Designation | Nucleotide | Amino Acid |
| Catalpa lysine decarboxylase | ncs.pk0009.a12 | 1 | 2 |
| Corn lysine decarboxylase | p0126.cnlbg13r | 3 | 4 |
| Soybean lysine decarboxylase | scr1c.pk003.m5 | 5 | 6 |
| Corn tyrosine decarboxylase | p0031.ccmba59r | 7 | 8 |
| Rice tyrosine decarboxylase | rls6.pk0031.b5 | 9 | 10 |
| Soybean tyrosine decarboxylase | sfl1.pk130.k18 | 11 | 12 |
| Wheat tyrosine decarboxylase | wr1.pk0059.g9 | 13 | 14 |
| Corn tryptophan decarboxylase | p0031.ccmay35rb | 15 | 16 |
| Rice tryptophan decarboxylase | rls72.pk0013.a6 | 17 | 18 |
| Wheat tryptophan decarboxylase | wlk1.pk0023.d11 | 19 | 20 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms. "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several amino acid decarboxylases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other lysine decarboxylases, tyrosine decarboxylases or tryptophan decarboxylases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of lysine, tyrosine, or tryptophan in those cells. Overexpression of any of these genes would result in an increase in accumulation of alkaloids. Overexpression of lysine decarboxylase will result in the accumulation of higher amounts of cadaverine which will result in an increased biosynthesis of anabasine, a potent agonsit on muscle and neuronal alpha-bungarotoxin-sensitive nicotinic receptors. This would present a prospective smoking habit therapy.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded amino acid decarboxylase. An example of a vector for high level expression of the instant polypeptides in a bacterial host is provided (Example 8).

Additionally, the instant polypeptides can be used as targets to facilitate design and/or identification of inhibitors of those enzymes that may be useful as herbicides. This is desirable because the polypeptides described herein catalyze various steps in alkaloid metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various catalpa, corn, rice, soybean and wheat tissues were prepared. The characteristics of the libraries are described below.

TABLE 2 cDNA Libraries from Catalpa, Corn, Rice, Soybean and Wheat

| Library | Tissue | Clone |
|---|---|---|
| ncs | *Catalpa speciosa* Developing Seed | ncs.pk0009.a12 |
| p0031 | Corn Shoot Culture | p0031.ccmay35rb<br>p0031.ccmba59r |
| p0126 | Corn Leaf Tissue From V8–V10 Stages*, Pooled, Night-Harvested | p0126.cnlbg13r |
| rls6 | Rice Leaf 15 Days After Germination, 6 Hours After Infection of Strain *Magaporthe grisea* 4360-R-67 (AVR2-YAMO); Susceptible | rls6.pk0031.b5 |
| rls72 | Rice Leaf 15 Days After Germination, 72 Hours After Infection of Strain *Magaporthe grisea* 4360-R-67 (AVR2-YAMO); Susceptible | rls72.pk0013.a6 |
| scr1c | Soybean Embryogenic Suspension Culture Subjected to 4 Vacuum Cycles and Collected 12 Hours Later | scr1c.pk003.m5 |
| sfl1 | Soybean Immature Flower | sfl1.pk130.k18 |
| wlk1 | Wheat Seedlings 1 Hour After Treatment With Herbicide** | wlk1.pk0023.d11 |
| wr1 | Wheat Root From 7 Day Old Seedling | wr1.pk0059.g9 |

*Corn developmental stages are explained in the publication "How a corn plant develops" from the Iowa State University Coop. Ext. Service Special Report No. 48 reprinted June 1993.
**Application of 6-iodo-2-propoxy-3-propyl-4(3H)-quinazolinone; synthesis and methods of using this compound are described in USSN 08/545, 827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DHIOB cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via -polymerase chain reaction using primers specific for vector sequences flanking the inserted cDNA sequences. Amplified insert DNAs or plasmid DNAs are sequenced in dye-primer -sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding amino acid decarboxylases were identified by conducting BLAST (Basic Local Alignment Search Tool; Altschul et al. (1993) *J. Mol. Biol.* 215:403410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Lysine Decarboxylase

The BLASTX search using the EST sequences from clones listed in Table 3 revealed similarity of the polypeptides encoded by the cDNAs to lysine decarboxylase from Synechocystis sp. (NCBI General Identifier No. 1651862). Shown in Table 3 are the BLAST results for individual ESTs ("EST"), or the sequences of the entire cDNA inserts comprising the indicated cDNA clones ("FIS"):

TABLE 3

BLAST Results for Sequences Encoding Polypeptides Homologous to Lysine Decarboxylase

| Clone | Status | BLAST pLog Score 1651862 |
| --- | --- | --- |
| ncs.pk0009.a12 | EST | 29.10 |
| p0126.cnlbg13r | FIS | 106.00 |
| scr1c.pk003.m5 | FIS | 48.40 |

The data in Table 4 represents a calculation of the percent identity of the amino acid sequences set forth in SEQ ID NOs:2, 4 and 6 and the Synechocystis sp. sequence (NCBI General Identifier No. 1651862).

TABLE 4

Percent Identity of Amino Acid Sequences Deduced From the Nucleotide Sequences of cDNA Clones Encoding Polypeptides Homologous to Lysine Decarboxylase

| SEQ ID NO. | Percent Identity to 1651862 |
| --- | --- |
| 2 | 52.8 |
| 4 | 39.1 |
| 6 | 34.6 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a catalpa, a corn and a soybean lysine decarboxylases. These sequences represent the first plant sequences encoding lysine decarboxylase.

Example 4

Characterization of cDNA Clones Encoding Tyrosine Decarboxylase

The BLASTX search using the EST sequences from clones listed in Table 5 revealed similarity of the polypeptides encoded by the cDNAs to tyrosine decarboxylases from *Petroselinum crispum, Papaver somniferum*, or a putative tyrosine decarboxylase from *Arabidopsis thaliana* (NCBI General Identifier Nos. 1174828, 3282523 and 4512701, respectively). Shown in Table 5 are the BLAST results for individual ESTs ("EST"), or the sequences of the entire cDNA inserts comprising the indicated cDNA clones ("FIS"):

TABLE 5

BLAST Results for Sequences Encoding Polypeptides Homologous to Tyrosine Decarboxylase

| Clone | Status | NCBI General Identifier No. | BLAST pLog Score |
| --- | --- | --- | --- |
| p0031.ccmba59r | EST | 1174828 | 35.52 |
| rls6.pk0031.b5 | FIS | 4512701 | >254.00 |
| sfl1.pk130.k18 | FIS | 3282523 | >254.00 |
| wr1.pk0059.g9 | FIS | 4512701 | 166.00 |

The data in Table 6 represents a calculation of the percent identity of the amino acid sequences set forth in SEQ ID NOs:8, 10, 12 and 14 and the *Petroselinum crispum, Arabidopsis thaliana* or *Papaver somniferum* sequences (NCBI General Identifier Nos. 1174828, 4512701 and 3282523, respectively).

TABLE 6

Percent Identity of Amino Acid Sequences Deduced From the Nucleotide Sequences of cDNA Clones Encoding Polypeptides Homologous to Tyrosine Decarboxylase

| SEQ ID NO. | Percent Identity | NCBI General Identifier No. |
| --- | --- | --- |
| 8 | 51.5 | 1174828 |
| 10 | 71.6 | 4512701 |
| 12 | 68.3 | 3282523 |
| 14 | 71.8 | 4512701 |

Sequence alignments and percent identity calculations were performed using the Megalign program of the LASER-GENE bioinformatics computing suite (DNASTAR Inc., Madison, Wis). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice, a soybean and a wheat tyrosine decarboxylase. These sequences represent the first corn, rice, soybean and wheat sequences encoding tyrosine decarboxylase.

Example 3

Characterization of cDNA Clones Encoding Tryptophan Decarboxylase

The BLASTX search using the EST sequences from clones listed in Table 7 revealed similarity of the polypeptides encoded by the cDNAs to tryptophan decarboxylase from *Catharanthus roseus* (NCBI General Identifier No. 118306). Shown in Table 7 are the BLAST results for individual ESTs ("EST"), or the sequences of the entire cDNA inserts comprising the indicated cDNA clones ("FIS"):

TABLE 7

BLAST Results for Sequences Encoding Polypeptides Homologous to Tryptophan Decarboxylase

| Clone | Status | BLAST pLog Score 118306 |
|---|---|---|
| p0031.ccmay35rb | EST | 80.40 |
| rls72.pk0013.a6 | FIS | 120.00 |
| wlk1.pk0023.d11 | FIS | 162.00 |

The data in Table 8 represents a calculation of the percent identity of the amino acid sequences set forth in SEQ ID NOs: 16, 18 and 20 and the Catharanthus roseus sequence (NCBI General Identifier No. 118306).

TABLE 8

Percent Identity of Amino Acid Sequences Deduced From the Nucleotide Sequences of cDNA Clones Encoding Polypeptides Homologous to Tryptophan Decarboxylase

| SEQ ID NO. | Percent Identity to 118306 |
|---|---|
| 16 | 58.7 |
| 18 | 50.9 |
| 20 | 50.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a rice and a wheat tryptophan decarboxylase. These sequences represent the first monocot sequences encoding tryptophan decarboxylase.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (Epicurian Coli XL-1 BlueT; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per μL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/pL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can

Example 8
Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 1 6° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 9
Evaluating Compounds for Their Ability to Inhibit the Activity of Amino Acid Decarboxylases The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fuised thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, general assays for amino acid decarboxylases are presented by Heerze et al. (1990) Anal. Biochem. 185:201–205 and Burns and Aberhart (1988) Anal. Biochem. 171:339–345.

What is claimed is:

1. An isolated nucleic acid fragment encoding a lysine decarboxylase having an amino acid sequence identity that is at least 80% when compared, using the Clustal method of alignment, to the amino acid sequence set forth in a member selected from the group consisting of SEQ ID NO: 2, SEQ ID NO: 4, and SEQ ID NO: 6, wherein the amino acid sequence encoded by said isolated nucleic acid fragment has the functional properties of the amino acid sequence set forth in SEQ ID NO: 2, SEQ ID NO: 4, or SEQ ID NO: 6.

2. The isolated nucleic acid fragment of claim 1 CA wherein the nucleic acid fragment is RNA.

3. The isolated nucleic acid fragment of claim 1 wherein the nucleotide sequence of the fragment comprises the sequence set forth in a member selected from the group consisting of SEQ ID NO:1, SEQ ID NO:3 and SEQ ID NO:5.

4. A chimeric gene comprising the nucleic acid fragment of claim 1 operably linked to at least one regulatory sequence.

5. A transformed host cell comprising the chimeric gene of claim 4.

6. The complement of the isolated nucleic acid fragment of claim 1.

7. The isolated nucleic acid fragment of claim 1, wherein the amino acid sequence identity is at least 90%.

8. The isolated nucleic acid fragment of claim 1, wherein the amino acid sequence identity is at least 95%.

* * * * *